United States Patent

Harris et al.

[11] Patent Number: 4,551,329
[45] Date of Patent: Nov. 5, 1985

[54] ORAL MEDICAMENT LOLLIPOP

[75] Inventors: Joan Harris, 2485 Meridian, Miami Beach, Fla. 33140; Thomas J. Michel, Miami, Fla.

[73] Assignee: Joan Harris, Miami Beach, Fla.

[21] Appl. No.: 572,464

[22] Filed: Jan. 20, 1984

[51] Int. Cl.[4] .................................... A01N 25/12
[52] U.S. Cl. ........................ 424/22; D1/102; D7/42; 424/14; 426/75; 426/134
[58] Field of Search .............. 424/14, 22; 426/134, 426/75; D1/102; D7/42; 24/91, 90 R; 43/36

[56] References Cited

U.S. PATENT DOCUMENTS

| D. 93,287 | 9/1934 | Reed | D1/102 |
|---|---|---|---|
| D. 117,455 | 11/1939 | Parr | D1/102 |
| D. 117,456 | 11/1939 | Parr | D1/102 |
| 1,430,642 | 10/1922 | Gross | 43/36 |
| 1,593,858 | 7/1926 | Venablf | D1/102 |
| 1,847,415 | 3/1932 | Snell | 426/134 |
| 1,915,614 | 6/1933 | Parker | 426/75 |
| 1,971,560 | 8/1934 | Guyon | 426/134 |
| 2,096,611 | 10/1937 | Ellestad | 426/75 |
| 2,246,778 | 6/1941 | Cahoon | 426/134 |
| 2,295,042 | 9/1942 | Llewellyn | 43/36 |
| 2,323,656 | 7/1943 | Helfenstein | 43/36 |
| 2,469,589 | 5/1949 | Barricini | 426/134 |
| 2,488,272 | 11/1949 | Davis | D7/42 |
| 2,508,560 | 5/1950 | Adams | 43/36 |
| 2,897,624 | 8/1959 | Yakel et al. | 43/36 |
| 3,172,179 | 3/1965 | Schafer | 24/91 |
| 3,264,115 | 8/1966 | Davis | 426/75 |
| 3,418,743 | 12/1968 | Halvorsen | 43/36 |
| 3,816,953 | 6/1974 | Hameen-Anttila | 43/36 |

FOREIGN PATENT DOCUMENTS 2441341  7/1980  France .................. 426/75

Primary Examiner—Ronald W. Griffin
Attorney, Agent, or Firm—Michael Ebert

[57] ABSTRACT

A handle-supported oral medicament in a lollipop format to facilitate chewing or sucking thereof without the risk of inadvertent aspiration of large pieces of the medicament or of its entire body. The handle is formed by a stick of resilient material looped into a single coil whose ends are extended forwardly to define a pair of spring arms terminating in enlarged ears, the body of the medicament being molded about the ears, thereby securing the handle thereto. Because the ears occupy a large internal region therein, even if the body is chewed into pieces, these will be small and not, therefore, lodge in the throat or block the airway. And should the medicament separate from the ears of the handle in the mouth of the patient, the released arms will then spring apart to thereby block entry of the handle into the throat.

6 Claims, 4 Drawing Figures

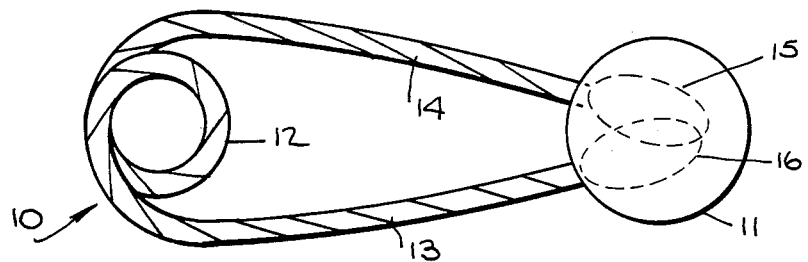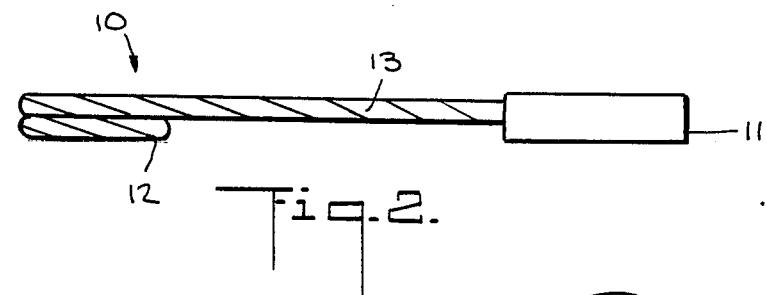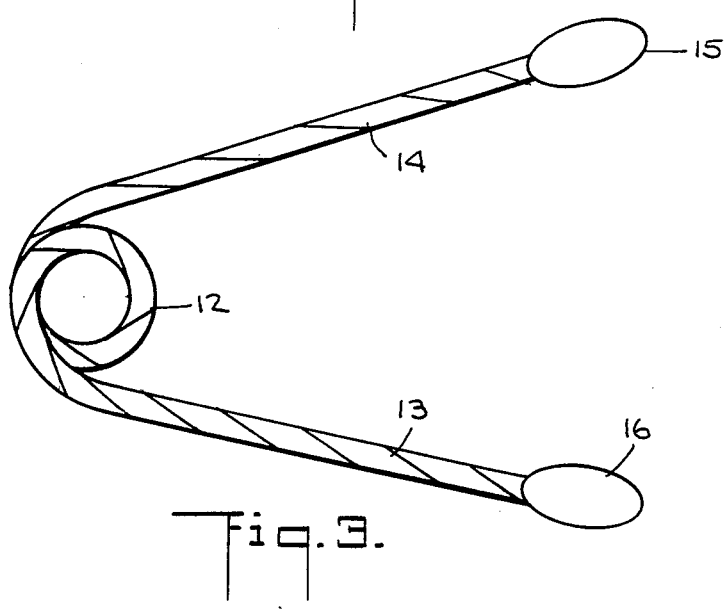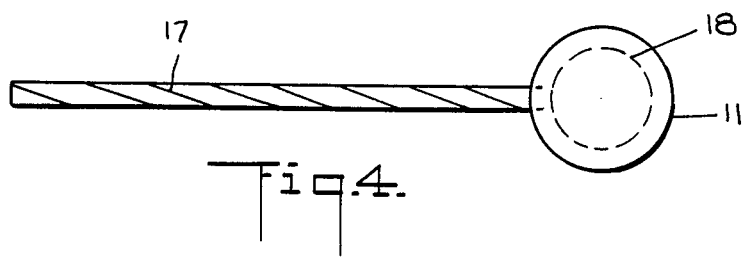

ORAL MEDICAMENT LOLLIPOP

BACKGROUND OF INVENTION

Field of Invention

This invention relates generally to oral medicaments in lump form which are suckable or chewable, and more particularly to a lumped medicament supported on a handle in a lollipop format to facilitate chewing or sucking thereof without the risk of inadvertent aspiration of large pieces of the medicament or of the entire body thereof.

By definition, a pill is medicine in a rounded mass which is small enough to be swallowed whole. The concern of the present invention is with oral medicaments in lump form which are larger than pills and are not intended to be swallowed whole but to be chewed or sucked to thereby more slowly administer a therapeutic agent. In this class of lumped medicaments, we find cough drops, throat lozenges, nasal sinus decongestants, various drugs for asthmatic conditions and other useful preparations.

Because lumped medicaments are retained in the mouth and are sucked or chewed therein, certain risks are entailed by this action, particularly with children and older patients. Thus, when a child is given a cough drop, he will suck it for a time; and when its size is reduced, he may proceed to break it up with his teeth and then swallow the jagged pieces. Should some of these pieces be fairly sizeable, they may lodge in the throat and choke the child. In other instances, a child may accidentally aspirate a large drop, and this may lead to serious medical consequences.

Similar problems are encountered with older patients or patients enfeebled as a result of serious illness, for these patients may lack the capacity to eject solids partially lodged in the air passage. Blockage of this passage may result in cardio-pulmonary collapse.

These problems can in some measure be obviated by supplying the lump medicament in a lollipop format; that is, by molding the body of the medicament on the end of a stick. There are obvious practical as well as psychological advantages in an oral medicament lollipop, for the patient can then suck or chew a prescribed medicine as if it were a piece of hard candy. There is little danger that the lump will be swallowed whole, as long as it is held on the stick. Moreover, since sucking a candy lollipop is normally a pleasurable activity, even if the medicament has a somewhat disagreeable flavor, this to some extent is mitigated by its psychological association with candy.

There are, however, a number of possible hazards which accompany the use of conventional lollipops, regardless of whether the lump on the stick is a hard candy or a medicament. Should the user accidentally fall on his face while holding the stick in his hand, this may push the stick into the throat; and should the lump break off from the stick, the exposed stick could then pierce the esophagus.

The prior art in the candy lollipop field recognizes these dangers and suggests as a solution thereto various forms of safety sticks. Thus the Cahoon U.S. Pat. No. 2,246,778 discloses a stick with a tapered neck that in case of an accident will break off. The Davis U.S. Pat. No. 3,264,115 shows a lollipop stick that is corrugated and will therefore bend when stressed, while the Guyon U.S. Pat. No. 1,971,560 proposes a bendable rubber safety stick for a lollipop.

The prior art is also addressed to the problem of more securely anchoring the hard candy to the stick of a lollipop. Thus the Snell U.S. Pat. No. 1,847,415 shows a stick whose end is provided with an enlarged head which is embedded in the lump of candy, while Venable, U.S. Pat. No. 1,593,858, discloses a bifurcated head at the end of the stick to render the coupling to the lump more secure.

SUMMARY OF INVENTION

In view of the foregoing, the main object of this invention is to provide a medicament lollipop with a safety handle adapted to facilitate sucking or chewing of the medicament by a patient without the risk of inadvertent aspiration of large pieces or of the entire body of the medicament.

More particularly, an object of this invention is to provide a medicament lollipop of the above type in which the handle is fabricated of resilient material so that should the user accidentally fall while holding the handle, the handle will absorb the impact and not transmit it to the lump with possible damage to tissue or to the teeth.

Also an object of the invention is to provide a safety handle for a lollipop which includes a pair of spring arms that are normally secured to the lump and which spring apart should the lump become separated from the handle, thereby preventing entry of the handle into the throat.

Yet another object of this invention is to provide an oral medicament lollipop that may be mass-produced at relatively low cost.

Briefly stated, these objects are attained in a handle-supported oral medicament in a lollipop format to facilitate chewing or sucking thereof without the risk of inadvertent aspiration of large pieces of the medicament or of its entire body. The handle is formed by a stick of resilient material looped into a single coil whose ends are extended forwardly to define a pair of spring arms terminating in enlarged ears, the body of the medicament being molded about the ears, thereby securing the handle thereto. Because the ears occupy a large internal region therein, even if the body is chewed into pieces, these will be small and not, therefore, lodge in the throat or block the airway. And should the medicament separate from the ears of the handle in the mouth of the patient, the released arms will then spring apart to thereby block entry of the handle into the throat.

OUTLINE OF DRAWINGS

For a better understanding of the invention as well as other objects and further features thereof, reference is made to the following detailed description to be read in conjunction with the accompanying drawings, wherein:

FIG. 1 is a plan view of an oral medicament lollipop in accordance with the invention;

FIG. 2 is a side view of the lollipop;

FIG. 3 shows the handle of the lollipop separated from the lumped medicament; and FIG. 4 is a simplified stick for the medicament.

DESCRIPTION OF INVENTION

Referring now to FIGS. 1 and 2, there is shown an oral medicament lollipop in accordance with the invention, the lollipop being constituted by a handle, generally designated by numeral 10, and a lumped medicament 11.

The nature of the medicament and its dosage obviously depends on its intended use; that is, whether it is a cold remedy, a decongestant or an antihistamine. In all instances, the formulation must be, as with a hard candy, in a moldable form when heated. In this way, the lumped medicament in the molten state can be injection molded about the ends of the handle and solidified in the mold so that the handle is securely attached to the mass.

In practice, dosimetry is based on the assumption that for a given medicament, the user receives a full single dose when the lollipop is fully consumed. Thus if a patient is to receive no more than four single doses per day, this fact is to be indicated on the packaging; for the lollipop is not a candy and care must be exercised, as with all drugs, to relate the dosage to the age and condition of the patient. It may be desirable in some instances to engrave the dosage on the molded lump, such as Two-A-Day.

Handle 10 is formed by a stick of resilient material having sufficient rigidity so that the handle is relatively stiff and not easily bent, For this purpose, use is preferably made of a stick formed of spirally-twisted paper which is moderately soft, yet fairly resilient. Alternatively, the stick may be fabricated from synthetic plastic material having properties comparable to spiralled paper.

The stick is looped to form a single turn coil 12 whose ends are extended forwardly to define a pair of spring arms 13 and 14 terminating in flattened ears 15 and 16. Because of the resilience of the stick material, coil 12 seeks to unwind and thereby cause arms 13 and 14 to spread apart.

In fabricating the lollipop, arms 13 and 14 are brought together to cause ears 15 and 16 to overlap, the lump 11 being molded about the overlapping heads which then occupy a relatively large region within the body of the medicament.

This arrangement has a three-fold advantage. First, because of the relatively large surface area of the overlapping ears, the area of adhesion to the lumped medicament is greater than with an ordinary narrow stick end, and the lump is therefore firmly anchored in the handle and cannot be separated therefrom while the lump is whole.

Second, when the patient chews on the lump, it can only break into fairly small pieces, for the internal ears create a core cavity within the lump, so that the mass of each piece does not include core material and is therefore small.

Third, when a point is reached where the lump is almost or fully consumed, this releases ears 15 and 16 which then spring apart. A similar action will take place as a result of an accidental impact causing the lump to break away from the ears. In either event, the ends of the handle cannot be pushed further into the mouth or into the throat of the patient, for the outspread arms prevent this action. Moreover, to the extent that contact is made with tissue within the mouth or with the teeth, this contact is cushioned or blunted by the enlarged ears and is not injurious in any way.

Instead of the arms of the handle extending from a coil, the arms may be defined by an uncoiled loop. Also, while a lumped medicament is shown in disc form, in practice it may be in any other shape, such as a rectangular tablet.

In a simplified version of the oral medicament as shown in FIG. 4, use is made of a straight stick 17 of spiralled paper terminating in a head 18 which may be spherical to occupy a large inner region in a lumped medicament which may also be spherical. In this arrangement, chewing of the medicament will cause the body thereof to break into small, safe pieces.

While there has been shown and described a preferred embodiment of an oral medicament lollipop in accordance with the invention, it will be appreciated that many changes and modifications may be made therein without, however, departing from the essential spirit thereof.

We claim:

1. A handle-supported oral mediament in a lollipop format to facilitate chewing or sucking thereof by a patient for therapeutic purposes without, however, exposing the patient to the inadvertent entry of the handle into his throat, said medicament comprising:

A. a lump of the medicament having a mass affording a full single dose of the medicament when fully consumed; and B. a safety handle having an enlarged end portion embedded in the lump which occupies a large internal region therein to securely anchor said lump and to prevent it from breaking into large pieces when chewed, said handle being formed of resilient stick material having a pair of spring arms whose enlarged end portions are embedded in the lump and are normally held under tension in the lump, said arms springing apart when the lump is detached from either arm in the course of its consumption or as a result of an accidental impact, whereby the handle cannot then be pushed further into the mouth or into the throat of the patient.

2. A medicament as set forth in claim 1, wherein said handle is defined by a single turn coil whose ends are extended to form said arms.

3. A medicament as set forth in claim 2, wherein said arms termiate inflattened ears which when secured to said lump are overlapped to occupy a central region therein.

4. A medicament as set forth in claim 1, wherein said stick material is spiral-twisted paper.

5. A medicament as set forth in claim 1, wherein said resilient stick is formed of synthetic plastic material.

6. A medicament as set forth in claim 1, wherein said lump is formed of a hard cough drop.

* * * * *

UNITED STATES PATENT OFFICE
CERTIFICATE OF CORRECTION

Patent No. 4,551,329                    Dated November 5, 1985

Inventor(s) Joan Harris

It is certified that error appears in the above-identified patent and that said Letters Patent are hereby corrected as shown below:

Column 4, line 47, after "terminate" insert a space between "in" and "flattened"

Signed and Sealed this

Eleventh Day of March 1986

[SEAL]

Attest:

DONALD J. QUIGG

Attesting Officer        Commissioner of Patents and Trademarks